(12) United States Patent
Liu

(10) Patent No.: US 11,235,006 B2
(45) Date of Patent: Feb. 1, 2022

(54) INHIBITING OR ALLEVIATING AGENT FOR Aβ-INDUCED DAMAGE

(71) Applicants: Jun Liu, Guangdong (CN); NIPPON ZOKI PHARMACEUTICAL CO., LTD., Osaka (JP)

(72) Inventor: Jun Liu, Guangzhou (CN)

(73) Assignees: Jun Liu, Guangdong (CN); NIPPON ZOKI PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 16/491,638

(22) PCT Filed: Mar. 6, 2017

(86) PCT No.: PCT/CN2017/075747
§ 371 (c)(1),
(2) Date: Sep. 6, 2019

(87) PCT Pub. No.: WO2018/161211
PCT Pub. Date: Sep. 13, 2018

(65) Prior Publication Data
US 2020/0289581 A1     Sep. 17, 2020

(51) Int. Cl.
*A61K 35/36*     (2015.01)
*A61P 25/28*     (2006.01)
*A61K 9/00*      (2006.01)

(52) U.S. Cl.
CPC ............ *A61K 35/36* (2013.01); *A61K 9/0019* (2013.01); *A61K 9/0053* (2013.01); *A61P 25/28* (2018.01)

(58) Field of Classification Search
None
See application file for complete search history.

(56) References Cited

U.S. PATENT DOCUMENTS

| | | | |
|---|---|---|---|
| 5,013,558 A * | 5/1991 | Konishi | A61P 25/28 424/520 |
| 2007/0032548 A1 | 2/2007 | Ellis | |
| 2011/0218242 A1 | 9/2011 | Ellis | |
| 2015/0119464 A1 | 4/2015 | Ellis | |

FOREIGN PATENT DOCUMENTS

| | | |
|---|---|---|
| CN | 101262863 A | 9/2008 |
| EP | 2364711 A1 | 9/2011 |

OTHER PUBLICATIONS

Fukuda, Yu et al., "Stimulated Neuronal Expression of Brain-Derived Neurotrophic Factor By Neurotropin", Molecular and Cellular Neuroscience, vol. 45, pp. 226-233, (2010).
Nakajo, Yukako et al., "ERV Enhances Spatial Learning and Prevents the Development of Infarcts, Accompanied by Upregulated BDNF in the Cortex", Brain Research; 1610, pp. 110-123, (2015).
Kimura, Hiroshi et al., "A Pilot Study for Clinical Applications of Neurotropin to Senile Patients With Dementia", Jpn Pharmacol Ther, vol. 15, No. 10, pp. 407-423, (1987).
Hoshino, Yuma et al., "Neurotropin Demonstrates Cytoprotective Effects in Lung Cells Through the Induction of Thioredoxin-1", Am J Resp. Cell Mol., vol. 37, pp. 438-446, (2007).
Kamo, Atsuko et al., "Neurotropin Suppresses Itch-Related Behavior in NC/NGA Mice With Atopic Dermatitis-Like Symptoms", Journal of Dermatological Science, vol. 81, No. 3, pp. 212-215, (Dec. 2016).
Shi, Xiaobing et al., "Preliminary Study on the Application of Neurotropin in Neurology Diseases", Chinese Journal of Pain Medicine, vol. 10, No. 6, pp. 371-372, (Dec. 2004).
Nov. 2, 2017 Search Report issued in International Patent Application No. PCT/CN2017/075747.
Nov. 2, 2017 Written Opinion issued in International Patent Application No. PCT/CN2017/075747.
Aug. 7, 2020 Extended European Search Report issued in European Patent Application No. 17899766.4.
Feb. 24, 2021 Office Action issued in Japanese Patent Application No. 2019-549471.
2. Brain Inflammation Hypothesis, Folia Pharmacol. Jpn; 150, pp. 141-147 (2017) (with partial translation).
Spangenberg et al., "Eliminating microglia in Alzheimer's mice prevents neuronal loss without modulating amyloid-β pathology," Brain. A Journal of Neurology, 139, pp. 1265-1281 (2016).

* cited by examiner

*Primary Examiner* — Susan Hoffman
(74) *Attorney, Agent, or Firm* — Oliff PLC

(57) ABSTRACT

An inhibiting or alleviating agent for amyloid beta (Aβ)-induced damage in hippocampus including an extract from inflamed tissues inoculated with vaccinia virus. Also relates to the use of the extract from inflamed tissues inoculated with vaccinia virus in the preparation of an agent for inhibiting or alleviating Aβ-induced damage in hippocampus.

7 Claims, 6 Drawing Sheets

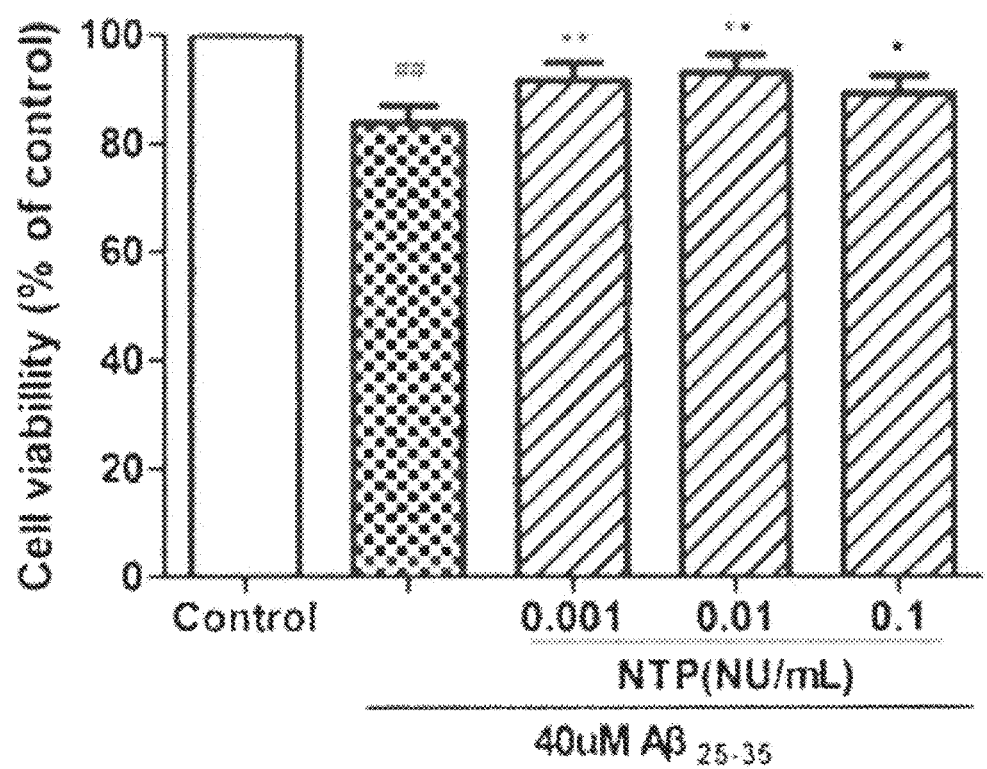
Figure 1 NTP inhibited Aβ25-35-induced decrease in cell viability.

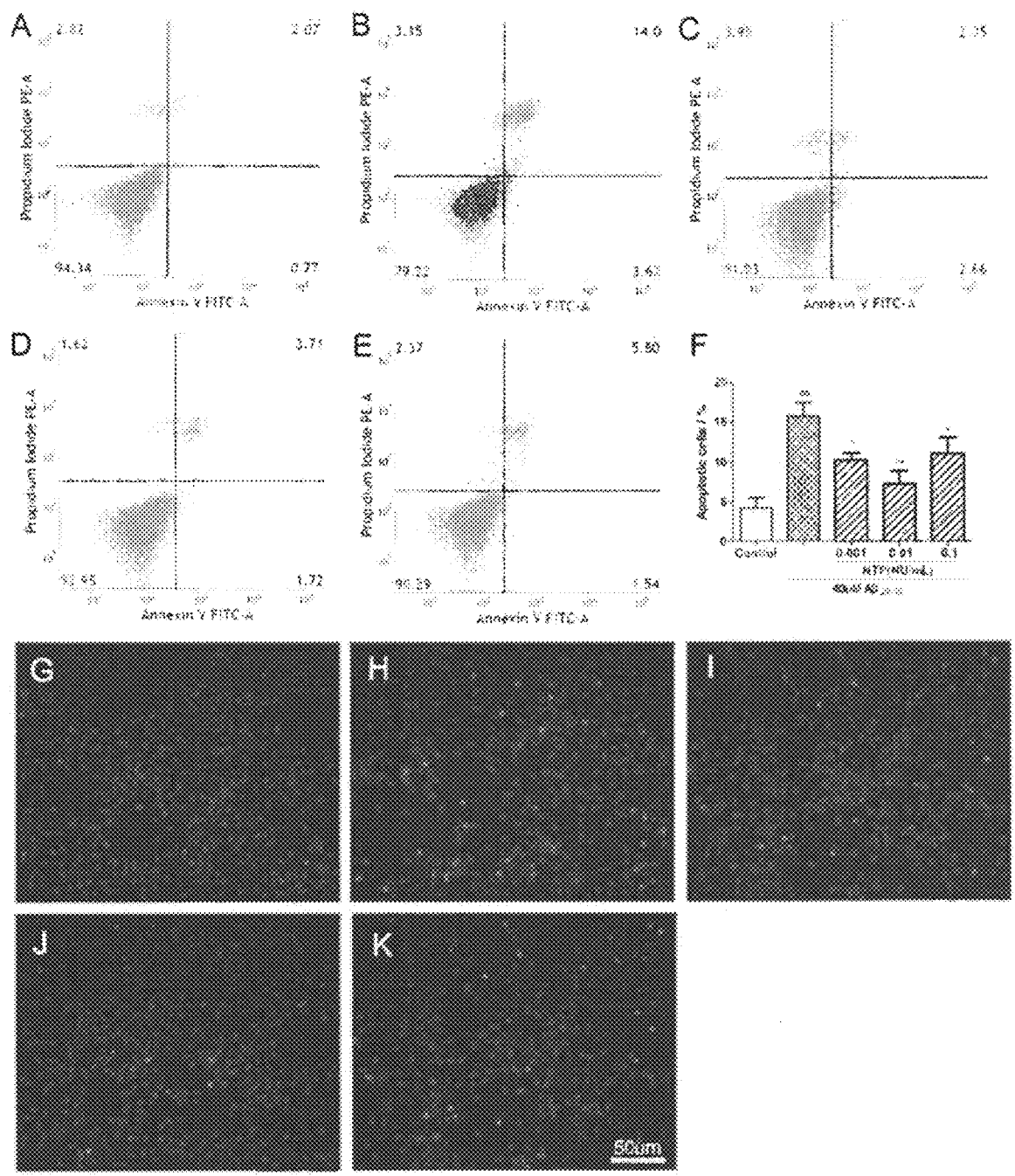
Figure 2 NTP alleviated Aβ$_{25-35}$-induced apoptosis.

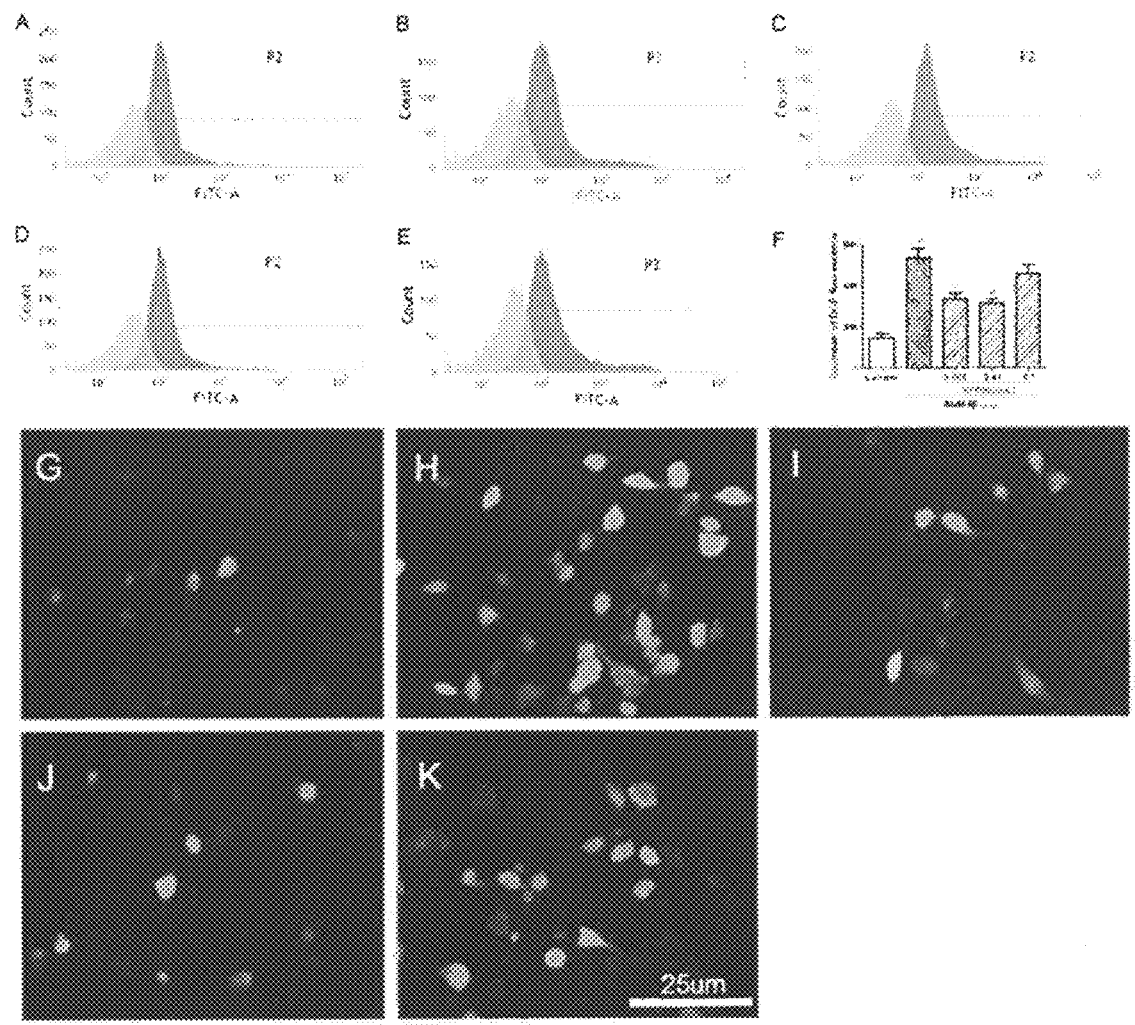
Figure 3 NTP ameliorated Aβ$_{25-35}$-induced intracellular ROS level.

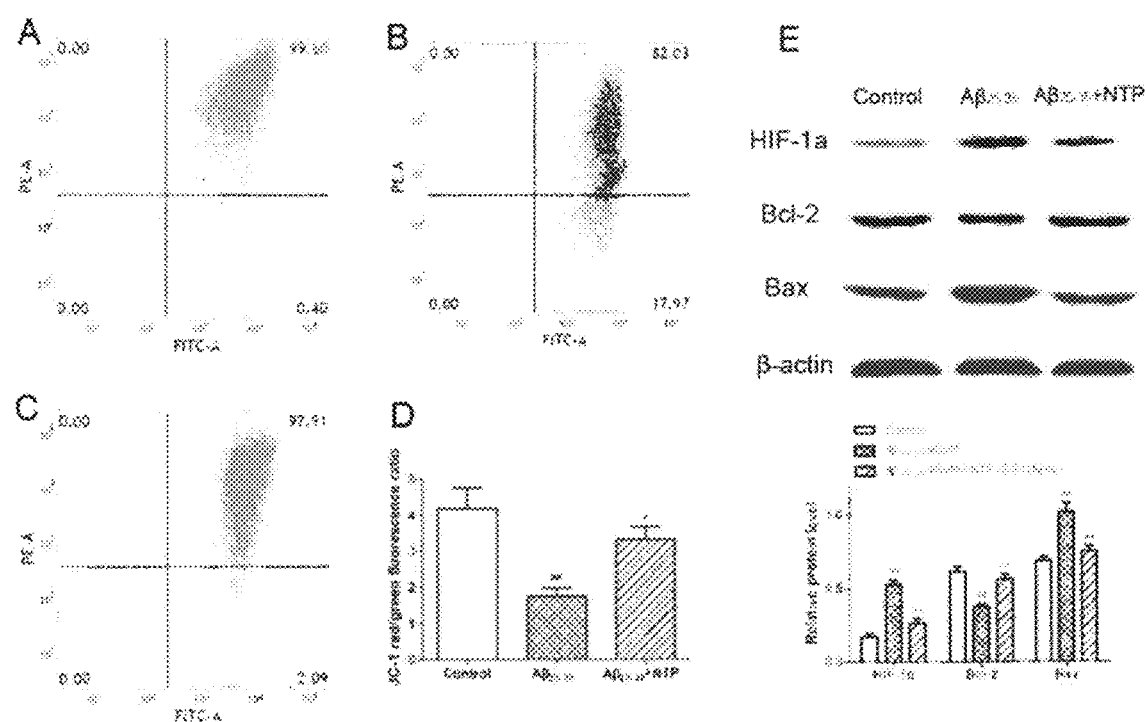
Figure 4 NTP improved MMP and affected the expression of HIF-1α and apoptosis-related molecules in HT22 cells.

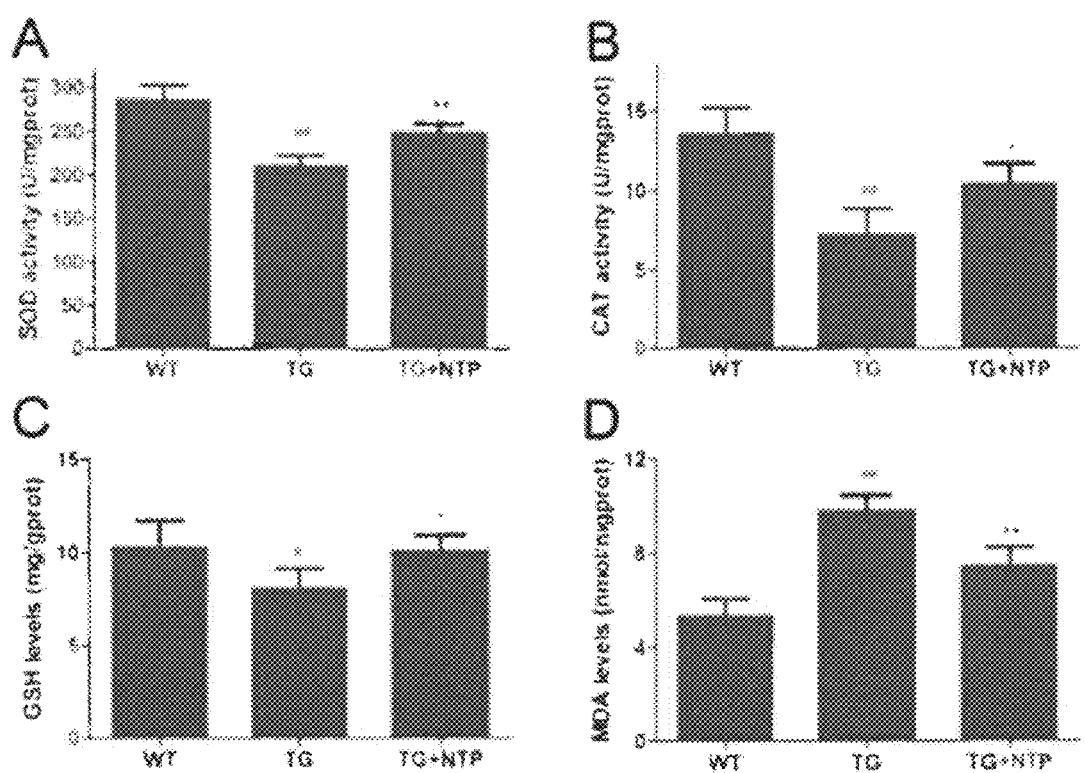
Figure 5 NTP regulated the activity of antioxidants in hippocampus of APP/PS1 mice.

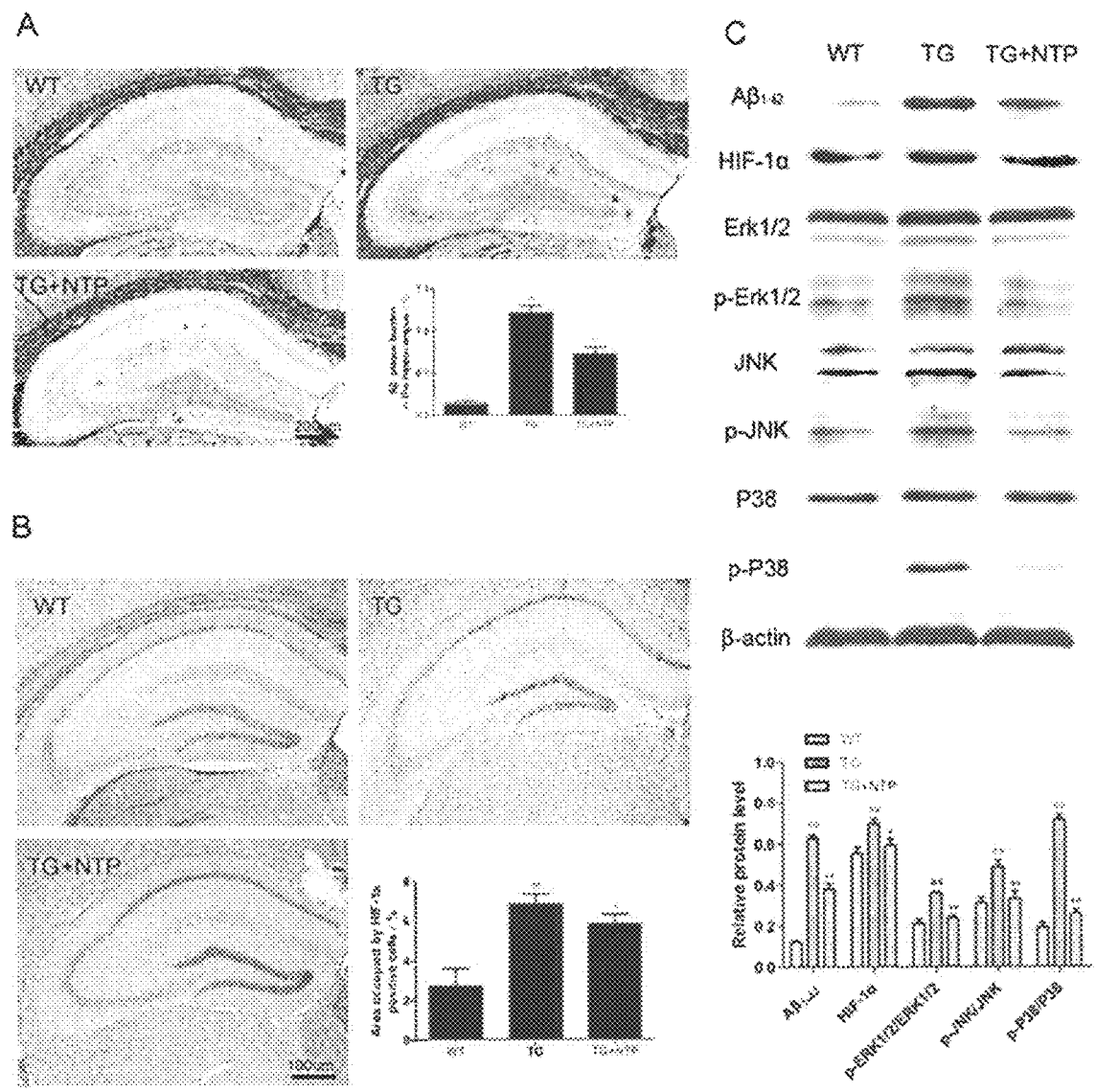
Figure 6 NTP suppressed Aβ deposition and activation of HIF-1α/MAPK pathway.

INHIBITING OR ALLEVIATING AGENT FOR Aβ-INDUCED DAMAGE

FIELD OF THE INVENTION

The present invention relates to an inhibiting or alleviating agent for amyloid beta (Aβ)-induced damage in hippocampus including an extract from inflamed tissues inoculated with vaccinia virus (hereinafter, it may be mentioned as "the extract").

BACKGROUND OF THE INVENTION

According to the 2016 World Alzheimer Report, the global population is aging at a rapid pace due to rising life expectancy. It's reported that there are 47 million people living with dementia worldwide and the number is projected to increase to more than 131 million by 2050. In China, the number is expected to rise to over 16 million by 2030. Clearly, the prevalence of dementia results in huge impacts on people's life quality and economy.

Alzheimer's disease (AD) is the most common progressive dementia among the elderly. Up to date, there are no effective anti-dementia drugs available for the management of AD due to its complex mechanisms. What's more, it's known that it will require enormous research costs and efforts for the discovery, development, and clinical trials for a new anti-dementia drug. For example, the search for Alzheimer's drug solanezumab ended in failure after spending millions on late-stage trials recently. Therefore, it is pretty necessary to reassess a promising current drug to halt the progressive cognitive dysfunctions with an established safety profile for AD.

Neurotropin (trademark; product of Nippon Zoki Pharmaceutical Co., Ltd.)(hereinafter mentioned as "NTP") is a well-known analgesic drug for treatment of chronic pain, such as low back pain, post herpetic neuralgia, neck-shoulder-arm syndrome, hyperesthesia of subacute myelo-optic neuropathy (SMON) and fibromyalgia containing the extract as an active ingredient. Recently, it's reported that NTP (Most experiments were conducted using experimental product containing the extract in higher concentration than commercial product "Neurotropin". However the word "the extract" is also used in such cases for convenience sake in this application.) stimulated BDNF expression in SH-SY5Y cells, and repeated oral administration of NTP (200 NU/kg/day for three months) inhibited the decline of hippocampal BDNF expression, accompanied by improvement of spatial cognition of Ts65Dn mice, a model of Down's syndrome (See Non-Patent Document 1). Furthermore, Nakajo et al. demonstrated that chronic NTP treatment reduced the volumes of infracted lesions, brain edema and the extent of the neurological deficits, and also enhanced spatial learning of C57BL/6J mice (See Non-Patent Document 2). A pilot study for clinical applications of NTP had shown that NTP was capable of improving clinical symptoms of senile patients with dementia (See Non-Patent Document 3). Besides, it's found by Hoshino et al. that NTP demonstrated cytoprotective effects against hydrogen peroxide and cigarette smoke through elevating the expression of redox-regulating molecules, glutathione peroxidase and catalase and, especially, thioredoxin-1. NTP also increased the cellular thioredoxin-1 content and regulated thioredoxin-1 release from cells, suppressing intracellular oxidative activity (See Non-Patent Document 4). Nevertheless, the potential antioxidative effect of NTP against neuronal damage remains to be determined. Besides, oxidative stress plays a crucial role in the pathogenetic mechanism for AD. Thus, we investigated the antioxidative capabilities of NTP on HT22 cells and APP/PS1 mice to obtain evidence for the administration of NTP for the treatment of AD.

In the present study conducted by the inventor(s) of this application (hereinafter mention as "this study"), we used immortalized murine hippocampal neurons (HT22 cells) as a cell model to explore whether NTP had potential capability to alleviate $Aβ_{25-35}$-induced neuronal damage. As reported, $Aβ_{25-35}$ is the shortest active fragment with similar neurotoxicity effect to a full-length Aβ. In addition, $Aβ_{25-35}$ can be easily synthesized and has been widely used in scientific researches. Thus, we choose this fragment in our research. In vivo, we examined the alterations of the activities of antioxidants and Aβ deposition in hippocampus of APP/PS1 mice after administration of NTP and further investigated the potential underlying mechanisms.

PRIOR ART DOCUMENTS

Non-Patent Documents

1. Fukuda Y, Berry T L, Nelson M, et al. Stimulated neuronal expression of brain-derived neurotrophic factor by Neurotropin. Mol Cell Neurosci 2010; 45:226-233.
2. Nakajo Y, Yang D, Takahashi J C, Zhao Q, Kataoka H, Yanamoto H. ERV enhances spatial learning and prevents the development of infarcts, accompanied by upregulated BDNF in the cortex. Brain Res 2015; 1610:110-123.
3. Kimura H, Nakamura S, Okamoto K, Toyama I, Watanabe M, Ikeuchi K. A pilot study for clinical applications of Neurotropin to senile patients with dementia. Jpn Pharmacol Ther 1987; 15: 407-423.
4. Hoshino Y, Nakamura T, Sato A, Mishima M, Yodoi J, Nakamura H. Neurotropin demonstrates cytoprotective effects in lung cells through the induction of thioredoxin-1. Am J Resp Cell Mol 2007; 37:438-446.

SUMMARY OF THE INVENTION

In one aspect, the invention relates to an agent comprising an extract from inflamed tissue inoculated with vaccinia virus as the active ingredient, characterized in that the agent has the function of inhibiting or alleviating Aβ-induced damage in hippocampus.

In another aspect, the invention also relates to a use of an extract from inflamed tissue inoculated with vaccinia virus in the preparation of an agent for inhibiting or alleviating Aβ-induced damage in hippocampus.

In a preferred embodiment, the Aβ-induced damage is oxidative damage. Alternatively, the Aβ-induced damage is induced by Aβ deposition.

In another preferred embodiment, the function of the agent is induced by the suppression of the expression of HIF-1α and/or Bax.

In still another preferred embodiment, the agent is an agent for prevention, alleviation or treatment of Alzheimer's disease.

In a further embodiment, the inflamed tissue is the skin tissue of rabbits.

In a still further embodiment, the agent is an injection agent or an oral agent.

BRIEF DESCRIPTION OF THE DRAWINGS

FIG. 1: HT22 cells were co-incubated with 40 μM $Aβ_{25-35}$ for 24 h after pretreatment with various concentrations of NTP for 16 h, following the evaluation of cell viability with CCK8 assays. Data were represented as relative percentage to the control group and shown as mean±SE (n=6). ##P<0.01 versus control, *P<0.05 and **P<0.01 versus $A\beta_{25-35}$ group.

FIG. 2: (A) Control group. (B) HT22 cells were exposed to 40 μM $A\beta_{25-35}$ for 24 h. (C-E) HT22 cells were co-incubated with 40 μM $A\beta_{25-35}$ for 24 h after pretreatment with various concentrations of NTP (0.001, 0.01, 0.1 UN/mL) for 16 h. Cell apoptosis was assessed by flow cytometry. (F) Statistical results of cell apoptotic rates. (G-K) HT22 cells were stained with Hoechst 33342 and propidium iodide (PI) and observed under a fluoroscent microscope after treatment. As demonstrated in the pictures, $A\beta_{25-35}$ induced apoptosis was characterized by condensed, intensely fluorescent nuclei. NTP® markedly reduced the number of apoptotic cells. Values were represented as relative percentage to the control group and shown as mean±SE (n=6). ##P<0.01 versus control, *P<0.05 and **P<0.01 versus $A\beta_{25-35}$ group.

FIG. 3: (A) Control group. (B) HT22 cells were treated with 40 μM $A\beta_{25-35}$ for 24 h. (C-E) HT22 cells were co-incubated with 40 μM $A\beta_{25-35}$ for 24 h after pretreatment with various concentrations of NTP (0.001, 0.01, 0.1 UN/mL) for 16 h. Cells were stained with H2DCFDA for 20 minutes, and cellular green fluorescence was measured using a flow cytometer. (F) Statistical results of DCF fluorescence intensity. (G-K) HT22 cells were stained with H2DCFDA for 20 minutes and cellular green fluorescence was detected under a fluoroscent microscope after treatment. Values were presented as mean±SE (n=6). ##P<0.01 versus control, *P<0.05 and **P<0.01 versus $A\beta_{25-35}$ group.

FIG. 4: (A) Control group. (B) HT22 cells were treated with 40 μM $A\beta_{25-35}$ for 24 h. (C) HT22 cells were pretreated with 0.01 UN/mL NTP for 16 h and then co-incubated with 40 μM $A\beta_{25-35}$ for 24 h. Mitochondrial membrane potential (MMP, $\Delta\Psi m_t$) was measured by JC-1 staining. (F) Statistical results of JC-1 red/green fluorescence ratio. (E) The protein expression of HIF-1α, Bcl-2 and Bax following treatment above. The results were shown as mean±SE from at least three independent experiments. ##P<0.01 versus control, *P<0.05 and **P<0.01 versus $A\beta_{25-35}$ group.

FIG. 5: NTP-treated (TG+NTP), control (TG) APP/PS1 transgenic mice and control wild type (WT) mice. Treated APP/PS1 mice received daily administration of NTP (200 NU/kg/day) for 3 months by oral gavage delivery. The control (TG) APP/PS1 transgenic mice and control wild type (WT) mice were treated with saline (0.9% NaCl). (A) Superoxide dismutase (SOD) activity. (B) Catalase (CAT) activity. (C) Glutathione (GSH) levels. (D) Malondialdehyde (MDA) levels. Data were presented as means±SE, n=6 hippocampus in each group. #P<0.05 and ##P<0.01 versus WT mice, *P<0.05 and **P<0.01 versus TG mice.

FIG. 6: (A) Aβ plaques were detected by Bielschowsky silver staining. (B) Quantification of HIF-1α using immunohistochemistry. (C) Western blots and quantitative analysis for HIF-1α, p-ERK1/2, p-JNK1/2, and p-P38. The results presented as means±SE from at least three independent experiments. ##P<0.01 versus WT mice, *P<0.05 and **P<0.01 versus TG mice.

MODE FOR CARRYING OUT THE INVENTION

Materials

As to basic extracting steps for the extract, the following steps are used for example.

(A) Inflamed skin tissues of rabbits, mice etc. by the intradermal inoculation with vaccinia virus are collected, and the inflamed tissues are crushed. To the crushed tissues an extraction solvent such as water, phenol water, physiological saline or phenol-added glycerin water is added to conduct an extracting treatment for several days. Then, the mixture is filtrated or centrifuged to give a crude extract (filtrate or supernatant) wherefrom tissue fragments are removed.

(B) The crude extract obtained in (A) is adjusted to acidic pH, heated and then filtered or centrifuged to conduct a deproteinizing treatment. After that, the deproteinized solution is adjusted to basic pH, heated and then filtered or centrifuged to give a deproteinized filtrate or supernatant.

(C) The filtrate or the supernatant obtained in (B) is adjusted to acidic pH and adsorbed with an adsorbent such as activated carbon or kaolin.

(D) An extraction solvent such as water is added to the adsorbent obtained in (C), the mixture is adjusted to basic pH and the adsorbed component is eluted to give an extract from inflamed skins of rabbits inoculated with vaccinia virus (the present extract).

Various animals which can be infected with vaccinia virus such as rabbit, bovine, horse, sheep, goat, monkey, rat, mouse, etc. can be used as an animal for vaccinating vaccinia virus and obtaining inflamed tissue. Among them, an inflamed skin tissue of a rabbit is preferable as an inflamed tissue.

Any rabbit may be used so far as it belongs to *Lagomorpha*. Examples thereof include *Oryctolagus cuniculus*, domestic rabbit (domesticated *Oryctolagus cuniculus*), hare (Japanese hare), mouse hare and snowshoe hare. Among them, it is appropriate to use domestic rabbit. In Japan, there is family rabbit called "Kato" which has been bred since old time and frequently used as livestock or experimental animal and it is another name of domestic rabbit. There are many breeds in domestic rabbit and the breeds being called Japanese white and New Zealand white are advantageously used.

Vaccinia virus used herein may be in any strain. Examples thereof include Lister strain, Dairen strain, Ikeda strain, EM-63 strain and New York City Board of Health strain.

More detailed description regarding the method of manufacturing the extract is described, for example, in the paragraphs [0024]~[0027], [0031], etc. of WO2016/194816.

$A\beta_{25-35}$ was synthesized by Shanghai Sangon Biological Engineering Technology & Services Co. (Shanghai, China). Fetal bovine serum (FBS), medium (DMEM), neurobasal medium, and N2 supplement were obtained from Gibco (New York, USA). A cell counting kit-8 (CCK-8) was acquired from Dojin Kagaku (Kumamoto, Kyushu, Japan). Apoptosis detection kit was purchased from eBioscience (San Diego, Calif., USA). A ROS detection kit and mitochondrial membrane potential assay kit with JC-1 were purchased from the Beyotime Institute of Biotechnology (Shanghai, China). Hoechst 33342 and propidium iodide (PI) were procured from Invitrogen/Life Technologies (Carlsbad, Calif., USA). SOD, GSH, MDA, and CAT kits were supplied by Jiancheng Bioengineering Institute (Nanjing, China). The following primary antibodies against p-Erk1/2, p-P38, p-JNK, Erk1/2, P38, JNK, Bcl-2, Bax and secondary antibody horseradish peroxidase- (HRP-) conjugated goat anti-rabbit IgG were obtained from Cell Signaling Technology (Danvers, Mass., USA).

The primary antibody against HIF-1α was obtained from Abcam (Cambridge, Mass., USA) and the primary antibody against $A\beta_{1-42}$ was purchased from Sigma-Aldrich (St.

Louis, Mo., USA). The chemiluminescent horseradish peroxidase substrate was purchased from Millipore (Billerica, Mass., USA). All other routine experimental supplies and reagents were acquired from Thermo Fisher, Invitrogen, and MR Biotech.

EXAMPLES (1) Cell Culture, Differentiation, $A\beta_{25-35}$ Preparation and Treatment The methods used for the culture and differentiation of HT22 cells have been previously described in detail (refer Liu J, Li L, and Suo W Z. HT22 hippocampal neuronal cell line possesses functional cholinergic properties. *Life Sci* 2009; 84:267-271, and Zhao Z Y, Luan P, Huang S X, et al. Edaravone protects HT22 neurons from $H_2O_2$-induced Apoptosis by Inhibiting the MAPK Signaling Pathway. *CNS Neurosci Ther* 2013; 19:163-169.). Briefly, HT22 cells were cultured in DMEM media supplemented with 10% FBS, 100 U/mL penicillin, and 100 ug/mL streptomycin, and differentiated in neurobasal medium with N2 supplement for 24 h before treatment. $A\beta_{25-35}$ was diluted in sterile saline at a concentration of 0.5 mM and was maintained at 37° C. for 7 days to pre-age the peptide. According to our previous study (refer Fan S, Zhang B, Luan P, et al. PI3K/AKT/mTOR/p70S6K Pathway is involved in $A\beta_{25-35}$-induced autophagy. *Biomed Res Int* 2015; 2015:1-9.), the viabilities of HT22 cells could significantly decrease when the cells were exposed to 40 µM $A\beta_{25-35}$ for 24 h. Thus, we selected 40 µM as the optimal concentration of $A\beta_{25-35}$ for our subsequent research. HT22 cells were preconditioned with specified doses of NTP for 16 hours and subsequently treated with or without 40 µM $A\beta_{25-35}$ for 24 h.

(2) Cytotoxicity Assays

A CCK-8 assay was applied to assess the viabilities of HT22 cells. Briefly, following different treatment interventions, 10 µL/well of CCK-8 reagent was added to the cells, after which HT22 cells were incubated for 1.5 h at 37° C. and 5% $CO_2$ in dark conditions. Absorbance of the samples was detected at 450 nm with a multifunctional microplate reader (SpectraMax M5, USA).

(3) Apoptosis Assay by Flow Cytometry (FCM)

Apoptotic cell death of HT22 cells was measured by flow cytometric analysis with annexin V-FITC and PI apoptosis detection kit as detailed previously (refer Zhao Z Y, Luan P, Huang S X, et al. Edaravone protects HT22 neurons from $H_2O_2$-induced Apoptosis by Inhibiting the MAPK Signaling Pathway. *CNS Neurosci Ther* 2013; 19:163-169.). Briefly, HT22 cells were washed twice using phosphate buffered saline (PBS) and incubated with annexin V-FITC and PI in binding buffer after 24-hour exposure to $A\beta_{25-35}$ in the presence or absence of NTP. The cell suspension was applied for flow cytometric analysis with a flow cytometer (FACSCalibur; BD, Franklin Lakes, N.J.). Ten thousand cells per sample were measured. In parallel with the flow cytometric analysis, Hoechst 33342 and PI staining were performed for morphological assessment. The HT22 cells were fixed with 4% paraformaldehyde for 10 min. After three rinses with PBS, the cells were stained with 5 mg/L Hoechst 33342 and 1 mg/L PI. Cells were observed under a fluorescent microscope (BX51WI, Olympus, USA).

(4) Measurement of Intracellular ROS Generation

Intracellular ROS were measured by an oxidation-sensitive fluorescent probe (DCFH-DA) as reported previously (refer Bao F X, Shi H Y, Qi L, et al. Mitochondrial Membrane Potential-dependent Endoplasmic Reticulum Fragmentation is an Important Step in Neuritic Degeneration. *CNS Neurosci Ther* 2016; 22:648-660.). In brief, HT22 cells were pretreated with NTP for 16 hours and then exposed to 40 µM $A\beta_{25-35}$ for 24 hours. After treatment, cells were collected by pipetting, washed twice with PBS, and incubated with 10 µM DCFH-DA at 37° C. for 20 min. Ten thousand cells per sample were detected using a FACSCalibur flow cytometer. The geomean fluorescence intensity in positive cells represents the level of ROS. In addition, the DCF fluorescence intensity was also observed under a fluorescent microscope.

(5) Estimation of the Mitochondrial Membrane Potential (MMP, $\Delta\Psi m_t$)

MMP was estimated using a mitochondrial membrane potential assay kit with JC-1 according to the manufacturer's instructions. After treated, cells were washed twice with PBS and then stained with 5 µl/mL JC-1 for 20 min at 37° C. After two rinses with JC-1 staining buffer, the cell suspension was collected and MMP was monitored using a flow cytometer. Approximately 10,000 events from each sample were used for flow cytometric analysis.

(6) Animals and Drug Administration

Six month-old male APP/PS1 transgenic mice were obtained from Jackson Laboratory (ME, USA) and were maintained with free access to food and water. All mice used in this study were handled according to the protocols approved by the Institutional Animal Care and Use Committee of Sun Yat-sen University. The subjects in this study consisted of six month-old APP/PS1 transgenic mice (TG, n=16) and wild-type littermates (WT, n=8). Animals were randomly assigned into three groups: NTP-treated (TG+NTP), control (TG) APP/PS1 transgenic mice and control wild type (WT) mice. Treated mice received daily administration of NTP (200 NU/kg/day) for 3 months by oral gavage delivery. The remaining mice were treated with saline (0.9% NaCl) as placebo control.

(7) Measurements of SOD, MDA, GSH and CAT

The activities of Superoxide Dismutase (SOD), Glutathione (GSH) and Catalase (CAT), as well as the contents of Malondialdehyde (MDA) were determined using the commercial kits according to the manufacturer's instructions. The tissues of hippocampus were homogenized by sonication in cold 0.9% NaCl (9 mL), centrifuged at 4000 g for 10 min at 4° C., and the supernatants were collected and stored at 80° C. for the subsequent analysis. Protein concentration in the supernatant was assessed using micro BCA protein assay kit.

(8) Bielschowsky Silver Staining and Immunohistochemistry

Bielschowsky silver staining was performed on fixed sections using the previously published method (refer Schwab C, Steele J C, McGeer P L. Dystrophic neurites are associated with the majority of early stage extracellular neurofibrillary tangles in parkinsonism dementia complex of Guam. *Acta Neuropathol* 1997; 94:486-492, and Schwab C, Hosokawa M, Mcgeer P L. Transgenic mice overexpressing amyloid beta protein are an incomplete model of alzheimer disease. *Exp Neurol* 2004; 188:52-64.). For immunohistochemical staining, the mice brain sections were stained with DAB kit according to the instructions of the manufacturer for peroxidase labeling. Images were acquired from a fluorescent microscope. The primary antibody used in immunohistochemical staining was mouse anti-HIF-1α (1:800; Abcam, MA, USA). The surface area of the senile plaques and HIF-1α positive cells were measured and compared as percentage of the dentate gyrus with Image J software.

(10) Western Blot Analysis

After treatment, HT22 cells were lysed with an appropriate amount of boiling, denaturing lysate buffer (1% SDS, 1 mM sodium orthovanadate, 10 mM Tris-Cl, pH 7.4) supplemented with a protease inhibitor cocktail. Sample proteins of mouse hippocampus were extracted in rapid immunoprecipitation assay buffer (50 mM Tris [pH 7.4], 150 mM NaCl, 1% Triton X-100, 1% sodium deoxycholate, 0.1% sodium dodecyl sulfate [SDS]). Western blotting and semi-quantitative analyses were performed by previously described procedures. Primary antibodies and dilution rates used were listed as follow: HIF-1α, 1:2000; Bcl-2, 1:1000; Bax, 1:1000; $A\beta_{1-42}$, 1:1000; p-JNK, 1:500; p-P38, 1:500; p-ERK1/2, 1:500; JNK, 1:1000; P38, 1:500; ERK1/2, 1:2000 and β-actin, 1:1000.

(11) Statistical Analysis

All data were expressed as mean±SE and all statistical analyses were carried out using the SPSS 16.0 software (SPSS Inc., Chicago, Ill., USA). One-way analysis of variance (ANOVA) with post hoc tests was used for analysis of variance between groups, and differences between groups were compared using Student's t-test. Differences were considered statistically significant at $P<0.05$.

(12) Results (i) In Vitro Neuroprotection by NTP

As shown in FIG. 1, pretreatment with NTP at various concentrations from 0.001 to 0.1 UN/mL suppressed cytotoxicity induced by $A\beta_{25-35}$ ($P<0.05$). Flow cytometric analysis of cell apoptosis demonstrated that the administration of NTP from 0.001 to 0.1 UN/mL could significantly inhibit cell apoptosis caused by $A\beta_{25-35}$ ($P<0.05$) (FIG. 2A-F). A similar effect was observed by fluorescent microscopy in Hoechst 33342 and PI staining (FIG. 2G-K). We next explored whether NTP alleviated ROS levels. NTP treatment decreased the geo-mean DCF fluorescence and the effect was markedly significant at the concentrations of 0.001 and 0.01 UN/mL, but no significant differences of ROS generation were observed at the dose of 0.1 UN/mL, suggesting that high concentration of NTP may have no effect on suppressing intracellular ROS generation (FIG. 3A-F). The observation of ROS level by fluorescent microscopy was consistent with the results obtained from flow cytometry (FIG. 3G-K). Moreover, JC-1 staining revealed that mitochondrial membrane potential was attenuated by 0.01 NU/mL NTP compared to the $A\beta_{25-35}$ group (FIG. 4A-D).

(ii) In Vitro NTP Regulation of HIF-1α and Apoptosis-Related Molecules

To further explore the mechanism of the neuroprotective capacity of NTP against $A\beta_{25-35}$ in HT22 cells, we then measured the protein expression of HIF-1α, Bcl-2 and Bax. As shown in FIG. 4E, western blot analysis revealed that NTP significantly enhanced the expression of Bcl-2. In contrast to Bcl-2 induction, NTP suppressed the expression of HIF-1α and Bax ($P<0.01$).

(iii) In Vivo Antioxidative Effect by NTP

Oxidative stress markers were assessed in the hippocampus of APP/PS1 mice treated with NTP.

Compared with the control APP/PS1 mice group, the administration of NTP increased levels of superoxide dismutase (SOD), catalase (CAT), glutathione (GSH) ($P<0.01$, $P<0.05$, $P<0.05$, respectively), and decreased Malondialdehyde (MDA) content in hippocampus of NTP-treated APP/PS1 mice ($P<0.01$) (FIG. 5), suggesting that NTP exhibited a capability of regulating the balance of antioxidant system.

(iv) In Vivo NTP Inhibition of AD Deposition in Hippocampus

To investigate the potential effect of NTP treatment on Aβ deposition in hippocampus of APP/PS1 mice, the coronal sections of hippocampus of control wide type mice, control and NTP-treated APP/PS1 mice were determined using Bielschowsky silver staining and hippocampal tissues were collected for the measurement of Aβ protein level. Quantification analysis showed that the surface area of Aβ plaque deposits decreased significantly in the NTP-treated group compared to the APP/PS1 mice group (FIG. 6A) ($P<0.01$). In accordance with this result, we observed a reduced level of $A\beta_{1-42}$ protein in hippocampus of NTP-treated group (FIG. 6C).

(v) In Vivo Suppression of HIF-1α and MAPK Family Activation by NTP

In order to further investigate the underlying mechanisms of the neuroprotective effects of NTP, we first detected the expression of HIF-1α in hippocampus by immunohistochemistry and western blot. Results showed that HIF-1α expression was inhibited in NTP-treated mice (FIG. 6B) ($P<0.05$). As shown in FIG. 6C, we also examined the activation of mitogen-activated protein kinase (MAPK) pathways using western blot analysis. Compared to the wide type group, we found that the phosphorylation of ERK1/2, JNK, and P38 was promoted in APP/PS1 mice. However, NTP treatment markedly decreased the expression of p-ERK1/2, p-JNK and p-P38 ($P<0.01$).

INDUSTRIAL APPLICABILITY

Our results from in vitro experimentation provided direct evidence of NTP protection against $A\beta_{25-35}$-induced oxidative damage and cell death. ROS levels and HIF-1α were significantly decreased in HT22 cells. Simultaneously, mitochondrial membrane potential was increased. In fact, mitochondrial function had been recognized as a pivotal role in AD pathogenesis. Mitochondria accumulate membrane damage could assist increased ROS production in cells and in an AD mouse model. Mitochondrial dysfunction was found to begin as early as three months. In particular, chen et al. demonstrated that mitochondrial injury induced by oxidative and nitrative stress could trigger the caspase cascades via the release of cytochrome c, leading to cell apoptosis in hippocampus. The findings from in vivo study showed us that NTP exerted a protective effect on enhancing the activities of antioxidants and reducing the formation of Aβ deposition. For further study of the mechanism of NTP, we investigated the expression of HIF-1α and stress-related mitogen-activated protein kinase (MAPK) signals. The MAPKs, a family of serine/threonine protein kinases, are key signaling pathways in modulation of cell growth, differentiation, and cell death. Aβ-induced oxidative stress could alter these cellular signaling pathways and induce phosphorylation responses in cells. An upregulation of activation of JNK and P38 had been implicated in AD brains and the MAPK signaling pathways could be activated in response to Aβ accumulation. Guo et al. observed that MAPKs signals could be activated by anisomycin and induce intracellular Aβ production in neuroblastoma cells. Therefore, the dysregulation of MAPK cascades further supports the pathological association between Aβ and oxidative stress in AD. In this study, we found an increased activation of ERK1/2, JNK, and P38 in APP/PS1 mice. However, activation of the MAPKs was reduced in NTP-treated APP/PS1 mice, indicating that the phosphorylation responses could be suppressed by NTP.

Taken together, our results demonstrated that $A\beta_{25-35}$ could induce hippocampal neuronal injury including the upregulation of ROS levels, the downregulation of mitochondrial membrane potential and the promotion of cell apoptosis. In contrast, NTP treatment could reverse the damage mediated by $A\beta_{25-35}$ in HT22 cells. Furthermore, NTP could ameliorate the deposition of Aβ plaques in hippocampus of APP/PS1 mice and modify the activities of antioxidants. The neuroprotective capability of NTP is likely to be associated with the suppression of HIF-1α and MAPK signaling pathways. In brief, NTP may act as a radical scavenger to be applied for the prevention and treatment of AD in the future.

What is claimed is:

1. A method for inhibiting or alleviating AP-induced damage in hippocampus by the suppression of the expression of HIF-1α, comprising administering an extract from inflamed tissues inoculated with vaccinia virus to a patient in need of the suppression of the expression of HIF-1α.

2. The method according to claim 1, wherein the Aβ-induced damage is oxidative damage.

3. The method according to claim 1, wherein the Aβ-induced damage is induced by AP deposition.

4. The method according to claim 1, wherein the inhibition or alleviation of Aβ-induced damage is further achieved by the suppression of the expression of Bax.

5. The method according to claim 1, wherein the patient has Alzheimer's disease.

6. The method according to claim 1, wherein the inflamed tissues are skin tissues.

7. The method according to claim 1, wherein the inflamed tissues are skin tissues of rabbits.

* * * * *